US012805895B2

(12) United States Patent
Rosa et al.

(10) Patent No.: US 12,805,895 B2
(45) **Date of Patent: *Nov. 24, 2026**

(54) SURGICAL INSTRUMENT CONTROL

(71) Applicant: INTUITIVE SURGICAL OPERATIONS, INC., Sunnyvale, CA (US)

(72) Inventors: David J. Rosa, San Jose, CA (US); Salvatore J. Brogna, Los Gatos, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 231 days.

This patent is subject to a terminal disclaimer.

(21) Appl. No.: 18/442,742

(22) Filed: Feb. 15, 2024

(65) Prior Publication Data

US 2024/0293139 A1 Sep. 5, 2024

Related U.S. Application Data

(63) Continuation of application No. 17/205,483, filed on Mar. 18, 2021, now Pat. No. 11,937,841, which is a (Continued)

(51) Int. Cl.
*A61B 34/30* (2016.01)
*A61B 17/32* (2006.01)
(Continued)

(52) U.S. Cl.
CPC ................ *A61B 17/320016* (2013.01); *A61B 18/1233* (2013.01); *A61B 18/1445* (2013.01);
(Continued)

(58) Field of Classification Search
CPC ........ A61B 17/320016; A61B 18/1206; A61B 18/1233; A61B 18/1445; A61B 18/1447;
(Continued)

(56) References Cited

U.S. PATENT DOCUMENTS 6,905,497 B2 6/2005 Truckai et al.
6,949,106 B2 9/2005 Brock et al.
(Continued)

OTHER PUBLICATIONS

Extended European Search Report for Application No. 13775566.6, mailed on Oct. 30, 2015, 7 pages (ISRG04570/EP).
(Continued)

*Primary Examiner* — Joseph A Stoklosa
(74) *Attorney, Agent, or Firm* — Jones Burke, PLLC

(57) ABSTRACT

A control system includes a processor communicatively coupled with first and second user-actuated input mechanisms. The processor is configured to, in response to a first input at the first user-actuated input mechanism, command a jaw mechanism of an end effector to move from an open position to an intermediate closed position within the range of motion of the jaw mechanism, and command a translating mechanism of the end effector to move from a proximal position to an intermediate position relative to the jaw mechanism. In response to a second input at the first user-actuated input mechanism, the processor is configured to command the jaw mechanism to move to the closed position, and command the translating element of the end effector to move from the intermediate position to the distal position.

20 Claims, 6 Drawing Sheets

Related U.S. Application Data continuation of application No. 16/292,947, filed on Mar. 5, 2019, now Pat. No. 10,966,742, which is a continuation of application No. 15/357,589, filed on Nov. 21, 2016, now Pat. No. 10,265,092, which is a continuation of application No. 14/866,268, filed on Sep. 25, 2015, now Pat. No. 9,504,517, which is a continuation of application No. 13/834,760, filed on Mar. 15, 2013, now Pat. No. 9,144,456.

(60) Provisional application No. 61/621,974, filed on Apr. 9, 2012.

(51) Int. Cl.

| | |
|---|---|
| ***A61B 18/12*** | (2006.01) |
| ***A61B 18/14*** | (2006.01) |
| ***A61B 34/35*** | (2016.01) |
| *A61B 17/00* | (2006.01) |
| *A61B 18/00* | (2006.01) |

(52) U.S. Cl.

CPC .......... *A61B 18/1447* (2013.01); *A61B 34/30* (2016.02); *A61B 34/35* (2016.02); *A61B 2017/00973* (2013.01); *A61B 2018/00601* (2013.01); *A61B 2018/0063* (2013.01); *A61B 18/1206* (2013.01); *A61B 2018/1455* (2013.01)

(58) Field of Classification Search

CPC ........... A61B 2017/00973; A61B 2018/00601; A61B 2018/0063; A61B 2018/1455; A61B 34/30; A61B 34/35

See application file for complete search history.

(56) References Cited

U.S. PATENT DOCUMENTS

| | | | | |
|---|---|---|---|---|
| 7,303,107 | B2 | 12/2007 | Milliman et al. | |
| 7,784,662 | B2 | 8/2010 | Wales et al. | |
| 7,861,906 | B2 | 1/2011 | Doll et al. | |
| 8,161,977 | B2 | 4/2012 | Shelton, IV et al. | |
| 9,144,456 | B2 | 9/2015 | Rosa et al. | |
| 9,504,517 | B2 | 11/2016 | Rosa et al. | |
| 10,265,092 | B2 | 4/2019 | Rosa et al. | |
| 10,966,742 | B2 | 4/2021 | Rosa et al. | |
| 11,937,841 | B2 | 3/2024 | Rosa et al. | |
| 2002/0133173 | A1 | 9/2002 | Brock et al. | |
| 2003/0114851 | A1 | 6/2003 | Truckai et al. | |
| 2003/0195664 | A1* | 10/2003 | Nowlin .................. | A61B 34/37 318/568.11 |
| 2008/0167522 | A1 | 7/2008 | Giordano et al. | |
| 2010/0179540 | A1* | 7/2010 | Marczyk ............ | A61B 18/1445 606/41 |
| 2010/0228250 | A1 | 9/2010 | Brogna | |
| 2011/0087256 | A1 | 4/2011 | Wiener et al. | |
| 2011/0155781 | A1 | 6/2011 | Swensgard et al. | |
| 2011/0240714 | A1 | 10/2011 | Whitman et al. | |
| 2011/0297729 | A1 | 12/2011 | Whitman et al. | |
| 2011/0301601 | A1 | 12/2011 | Garrison et al. | |
| 2012/0006880 | A1 | 1/2012 | Whitman et al. | |
| 2012/0022519 | A1 | 1/2012 | Huang et al. | |
| 2012/0022524 | A1 | 1/2012 | Timm et al. | |
| 2012/0205419 | A1 | 8/2012 | Weir et al. | |
| 2012/0209288 | A1 | 8/2012 | Robinson | |
| 2012/0209314 | A1 | 8/2012 | Weir et al. | |
| 2012/0215220 | A1 | 8/2012 | Manzo et al. | |
| 2012/0248167 | A1 | 10/2012 | Flanagan et al. | |
| 2013/0103050 | A1 | 4/2013 | Richmond et al. | |
| 2021/0275207 | A1 | 9/2021 | Rosa et al. | |

OTHER PUBLICATIONS

Extended European Search Report for Application No. EP17188031.3, mailed on Jan. 8, 2018, 7 pages (ISRG04570D1/EP).

Extended European Search Report for Application No. EP22160757, mailed on Jul. 5, 2022, 10 pages.

International Search Report and Written Opinion for Application No. PCT/US2013/035479, mailed on Jul. 11, 2013, 11 pages (ISRG04570/PCT).

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

Extended European Search Report for Application No. EP26188939.8, mailed on Sep. 15, 2026, 14 pages.

* cited by examiner

SURGICAL INSTRUMENT CONTROL

CROSS-REFERENCE TO RELATED APPLICATIONS

This application is a continuation of U.S. application Ser. No. 17/205,483, filed Mar. 18, 2021, which is a continuation of U.S. application Ser. No. 16/292,947, filed Mar. 5, 2019 (now U.S. Pat. No. 10,966,742), which is a continuation of U.S. application Ser. No. 15/357,589, filed Nov. 21, 2016 (now U.S. Pat. No. 10,265,092), which is a continuation of U.S. application Ser. No. 14/866,268, filed Sep. 25, 2015 (now U.S. Pat. No. 9,504,517), which is a continuation of U.S. application Ser. No. 13/834,760, filed Mar. 15, 2013 (now U.S. Pat. No. 9,144,456), which claims priority to U.S. Provisional Patent Application No. 61/621,974, filed on Apr. 9, 2012, each of which is incorporated herein by reference in its entirety.

TECHNICAL FIELD

Aspects of the present disclosure concern surgical instrument control, and more particularly concern safe control of a surgical instrument cutting function.

INTRODUCTION

Certain hand-operated surgical tools use an I-beam shaped component to slide over and compress jaws together in order to provide a uniform compressive force on tissue to be fused. As the component slides over the jaws, the component's leading edge cuts tissue held between the jaws. An example of such a tool is a rounded tip Enseal® tissue sealer using I-Blade® technology, as commercialized by Ethicon Endo-Surgery, Inc.

Since the same moving component is used to close the jaws, compress the tissue between the jaws, and cut the compressed tissue, it is possible to inadvertently cut tissue while closing the jaws in a simple tissue grasping operation, or to cut tissue ahead of a complete tissue fusing. To prevent such inadvertent cutting, a movable mechanical stop is used to prevent the component from moving beyond its jaw closure function and into its cutting function. If an operator fails to properly set the mechanical stop, however, tissue grasped between the jaws may be partially cut, either with or without the application of electrosurgical tissue fusing energy. The result is that a patient is needlessly injured (e.g., tissue is inadvertently cut during grasping; tissue intended to be fused is cut before fusing is complete, with resulting bleeding; etc.). In addition, during minimally invasive surgery, controlling bleeding that may result from such an inadvertent cutting or incomplete fusing may be difficult and time consuming, exposing the patient to further risk. What is needed, therefore, is a way to take advantage of the benefits of the jaw closure, clamping, and cutting mechanism while preventing the risk of inadvertent cutting.

SUMMARY

The present teachings may solve one or more of the above-mentioned problems and/or may demonstrate one or more of the above-mentioned desirable features. Other features and/or advantages may become apparent from the description that follows.

In accordance with various exemplary embodiments, the present teachings contemplate a computer-controlled surgical system that comprises a surgical instrument having a working end and a control system configured to separately control a grasping function of the working end and a cutting function of the working end. The control system can be operatively connected to a first input device for controlling the grasping function of the working end and can be operatively connected to a second input device for controlling the cutting function of the working end.

In accordance with various exemplary embodiments, the present teachings contemplate a method of controlling multiple functions of a working end of a computer-controlled surgical instrument. The method comprises controlling a clamping function of the working end of the instrument in response to input received from a first input device. The method further comprises separately controlling a cutting function of the working end of the instrument in response to input received from a second input device.

Additional objects and advantages of the present teachings will be set forth in part in the description which follows, and in part will be obvious from the description, or may be learned by practice of the present disclosure and/or claims. At least some of those objects and advantages of the present disclosure will be realized and attained by means of the elements and combinations particularly pointed out in the appended claims.

It is to be understood that both the foregoing general description and the following detailed description are exemplary and explanatory only and are not restrictive of the present disclosure and claims, which are entitled to their full breadth of scope including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1A:
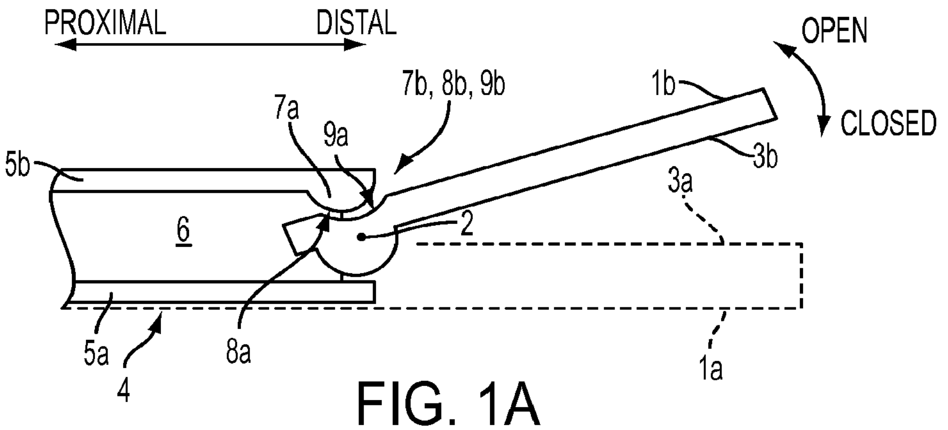
FIGS. 1A to 1E are diagrammatic plan views of a jaw closure and tissue cutting mechanism in accordance with the present teachings.

This description and the accompanying drawings that illustrate exemplary embodiments should not be taken as limiting, with the claims defining the scope of the present disclosure. Various mechanical, compositional, structural, electrical, and operational changes may be made without departing from the scope of this description and the present teachings as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained by the present teachings. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

In accordance with various exemplary embodiments, the present disclosure contemplates a surgical instrument, such as an electrosurgical instrument, that includes a shaft and a working end (end effector). The working end of the instrument includes components operable to perform gripping, cutting, and fusing procedures. The surgical instrument may be a hand-operated surgical instrument or an instrument in a telerobotic surgical system. The present disclosure contemplates that such a surgical instrument is operatively connected to a computer control system that independently controls each of the gripping, cutting, and fusing procedures of the instrument based on separate inputs. To initiate a desired function, the operator must select the appropriate input control function.

The present disclosure further contemplates that a single component of the working end of the instrument may be used to control both the gripping and cutting procedures through, for example, control of first and second ranges of motion of the component. Control of the energy application for the fusing procedure may be through individually received inputs or via the system computer in response to a system input. The present disclosure further contemplates that two procedures, although independently controlled, may be initiated at the same time in an automated manner. For example, the cutting and energy application functions may be simultaneously started after tissue is grasped to permit substantially simultaneous fusing and cutting of the tissue in an automatic process.

FIGS. 1A to 1E are diagrammatic plan views of a working end of a surgical instrument including a jaw closure and tissue cutting mechanism. Details of such a mechanism are described in, for example, U.S. Pat. No. 6,905,497 B2, entitled "Jaw Structure for Electrosurgical Instrument" (filed May 31, 2003) and U.S. Patent Application Pub. No. 2003/0114851 A1, entitled "Electrosurgical Jaws for Controlled Application of Clamping Pressure" (filed Dec. 13, 2001), both of which are incorporated herein by reference in their entirety. The following description highlights features associated with the present teachings. It should be understood that aspects of the present disclosure may be implemented with the various details shown in these two references (e.g., two movable jaws, one fixed and one movable jaw, jaws allowed to move apart slightly near the jaw fulcrum, etc.). It should be further understood that although the description below is in the context of an electrosurgical tool that fuses and cuts tissue, the same aspects may be applied to other instruments that may use a similar jaw closure and cutting architecture, such as surgical staplers.

FIG. 1A shows a set of jaws 1*a* and 1*b*. Jaw 1*a* (shown in phantom line to more clearly illustrate operating features) is fixed in position with reference to the distal end of a surgical instrument shaft (not shown), and jaw 1*b* pivots with reference to jaw 1*a* at fulcrum 2 so that the inner faces 3*a*, 3*b* of the jaws face each other when the jaws are closed. Electrodes (FIG. 2) configured to receive electrosurgical energy for tissue fusing are positioned on the jaws and in one implementation form a part of the inner faces 3*a*, 3*b*.

Figure 1B:
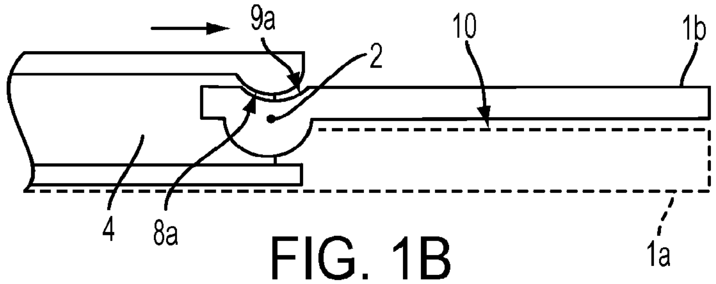
Figure 1C:
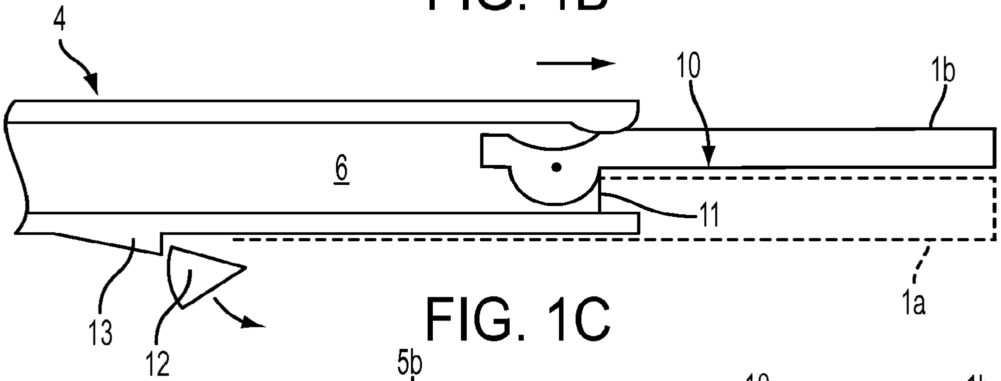
Figure 1D:
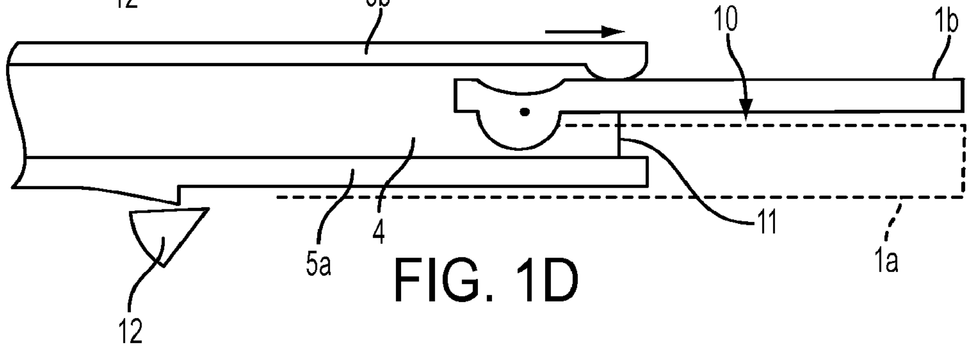
Figure 1E:
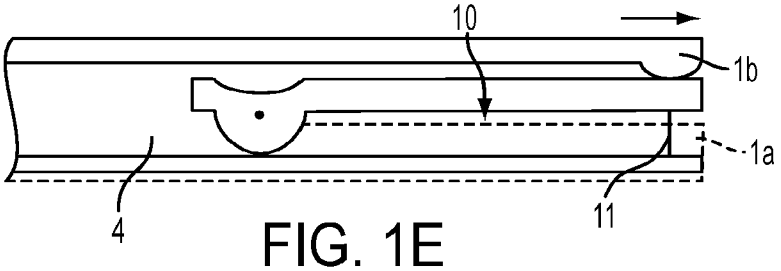

A reciprocating element 4 is movable relative to jaws 1*a*, 1*b*, between a full proximal position (see FIG. 1A) and a full distal position (see FIG. 1E). The reciprocating element 4 performs two functions. First, the reciprocating element 4 closes the jaws together. In the depicted implementation, reciprocating element 4's cross section is I-shaped, so that at least the distal part of reciprocating element 4 is shaped as an I-beam. As such, reciprocating element 4 includes a lower jaw closure flange 5*a*, an upper jaw closure flange 5*b*, and a connecting web 6 that connects the two flanges 5*a*, 5*b*. At the distal end of reciprocating member 4, upper jaw closure flange 5*b* is extended to include two shoulder elements 7*a* and 7*b* (hidden behind 7*a*). These shoulder elements 7*a*, 7*b* include cam surfaces 8*a*, 8*b* that engage with corresponding cam surfaces 9*a*, 9*b* on jaw 1*b*.

It can be seen from FIG. 1A that as reciprocating element 4 moves in a proximal direction to a full proximal position, as indicated by the arrow, cam surfaces 8*a*, 8*b* engage with corresponding cam surfaces 9*a*, 9*b*, which causes jaw 1*b* to pivot around fulcrum 2 towards an open position as shown. Similarly, as shown in FIG. 1B, as reciprocating element 4 moves in a distal direction towards the end tip of the instrument, as shown by the arrow, cam surfaces 8*a*, 8*b* engage with corresponding cam surfaces 9*a*, 9*b* to pivot jaw 1*b* around fulcrum 2 towards a closed position. In the closed position, a small gap 10 exists between jaw 1*a* and jaw 1*b*. Tissue to be fused and cut is held in gap 10 between the two jaws 1*a*, 1*b*.

FIG. 1C shows that as reciprocating element 4 moves distally from the position shown in FIG. 1B, a clamping force begins to be applied to tissue between the jaws 1*a*, 1*b*. The clamping force is initially from the jaws being compressed between shoulder elements 7_a_, 7_b_ and lower jaw closure flange 5_a_. At the near-proximal position illustrated in FIG. 1C, this clamping force is small. The clamping force becomes uniformly applied along the length of the jaws as the jaw closure flanges 5_a_, 5_b_ move along the jaws, as shown in FIGS. 1D and 1E.

FIG. 1C also illustrates reciprocating element 4's second function, which is to cut tissue clamped between the jaws 1_a_, 1_b_. As shown, the distal edge 11 of web 6 is a tissue cutting blade. Alternatively, edge 11 represents an electrosurgical energy cutting element as described in more detail in the references above. It can be seen that as reciprocating element 4 moves distally, blade 11 enters gap 10 and will cut any tissue securely held between jaws 1_a_, 1_b_. To prevent inadvertent cutting, therefore, a mechanical stop 12 engages part 13 of reciprocating element 4 to limit reciprocating element 4's distal travel and resultant tissue cutting. Alternatively, a similar mechanical stop may engage another component that causes reciprocating element 4 to move.

FIG. 1D shows that if stop 12 is moved away from engaging reciprocating element 4, then reciprocating element 4 may continue to move distally. Blade 11 enters gap 10 and cuts tissue grasped between jaws 1_a_, 1_b_. At the same time, upper and lower jaw closure flanges 5_a_, 5_b_ begin to apply a high clamping force against the jaws and consequently against the tissue held between the jaws in gap 10.

FIG. 1E shows reciprocating element 4 at a full distal position, at which a high and uniform clamping force is applied to jaws 1_a_ and 1_b_. At the position shown in FIG. 1E, blade 11 has cut any tissue in gap 10, and the necessary high clamping force has been applied to the tissue in gap 10 to enable an application of electrosurgical energy for successful tissue fusing.

It can be seen that reciprocating element 4 is representative of similar implementations in other devices. For example, it is known that linear surgical staplers use a sled that translates along a staple cartridge to force staples through tissue for formation against an anvil, which is typically a jaw similar in concept to jaw 1_b_. A tissue cutter, such as a knife blade, is fixed to the sled and cuts tissue clamped between the staple cartridge and anvil in a manner similar in concept to blade 11. If a portion of the reciprocating element is configured to bend (e.g., in a single degree of freedom orthogonal to the plane of jaw closure), then the surgical tool can be implemented with a distal end wrist capability to facilitate maneuverability inside the body, such as during minimally invasive surgery (e.g., laparoscopic or thoracoscopic surgery). Wrist aspects are discussed in more detail below. Alternatively, a portion of the reciprocating element may be allowed to flex with a more gradual bend, so that the shaft between an actuator and the surgical end effector may be made flexible.

Figure 1F:
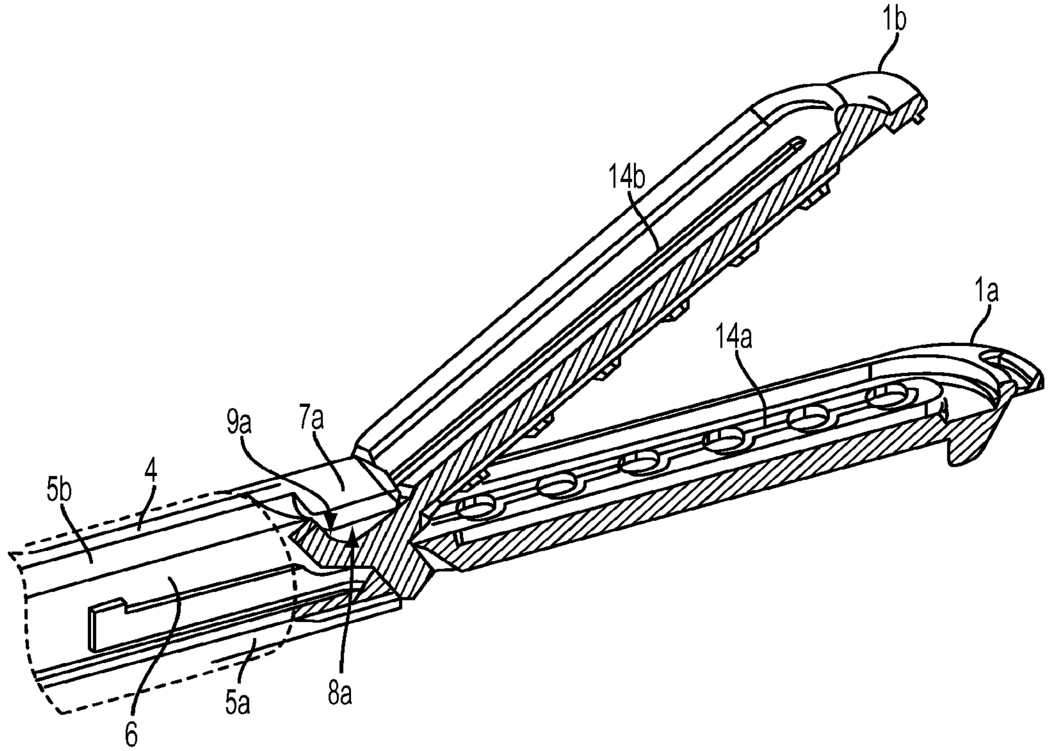
FIG. 1F is a perspective cutaway view of an embodiment of the mechanism illustrated in FIGS. 1A to 1E in accordance with the present teachings.

FIG. 1F is a perspective cutaway view of an embodiment of the surgical instrument working end mechanism illustrated in FIGS. 1A to 1E. FIG. 1F shows an exemplary embodiment in which cam surfaces 8_a_ and 9_a_ interact to open and close the jaws 1_a_, 1_b_. FIG. 1F also shows how lower and upper jaw closure rails 5_a_, 5_b_ slide along the jaws 1_a_, 1_b_ to clamp the jaws together. Finally, FIG. 1F shows that web 6 slides through slot 14_a_ in jaw 1_a_ and slot 14_b_ in jaw 1_b_ as reciprocating element 4 moves distally. Thus tissue cut by blade 11 (hidden from view) at the distal end of web 6 remains clamped between the two jaws 1_a_, 1_b_.

Figure 2:
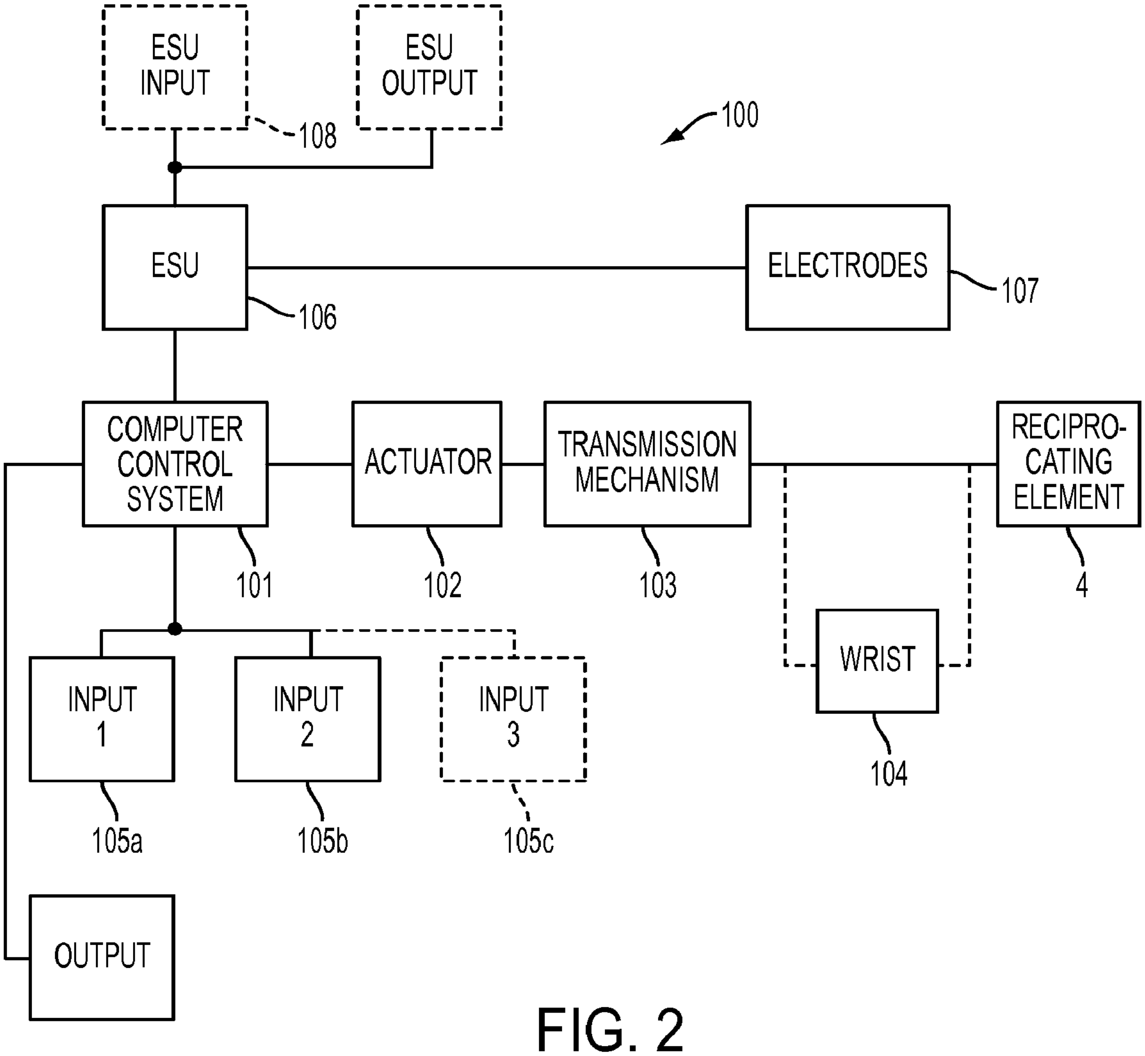
FIG. 2 is a diagrammatic view of a computer-controlled surgical system in accordance with the present teachings.

FIG. 2 is a diagrammatic view of an exemplary embodiment of a computer-controlled surgical system 100 in accordance with an aspect of the present disclosure. In one implementation, surgical system 100 is a general purpose telerobotic surgical system, such as the da Vinci® Si™ Surgical System commercialized by Intuitive Surgical, Inc., Sunnyvale, California. In another implementation, surgical system 100 is a hand-held tool similar to current hand-held electrosurgical or stapling tools, such as the powered iDrive™ stapler commercialized by Covidien AG and the hand-actuated EnSeal® tissue sealing devices commercialized by Ethicon Endo-Surgery, Inc. Persons familiar with robotic and medical device engineering will understand many of the routine mechanical and medical device implementation details, which are omitted from this description to avoid prolix explanation.

Surgical system 100 includes a computer control system 101 that controls system 100 operations in whole or in part. Computer control means control by any device that performs computations to effect such control, and it includes, by way of non-limiting example, control using a microprocessor, a microcontroller, a digital signal processor, a field programmable gate array, a programmable logic device, an optical computer, or any other form of programmable control that performs computations. Shared control occurs when part of the control is done by computer control, and part of the control is done by other means, such as manual operation. Control system 101 is configured to carry out one or more of the various implementations described herein.

Actuator 102 (e.g., a telerobotic slave servo actuator, an electric motor in a hand held tool, and the like) is coupled to and controlled by control system 101. In turn, reciprocating element 4 is coupled to actuator 102 via transmission mechanism 103, so that actuator moves reciprocating element 4 proximally and distally as described herein. Transmission mechanism 103 may include various mechanical devices such as levers, cams, gears, or lead screws in order to transmit actuation force and/or torque from actuator 102 to reciprocating element 4. An example of shared control is if movement of reciprocating element 4 is controlled over one range of travel as a result of computer control, and controlled over a second range of travel as a result of manual control (the actuator 102 being, in effect, two separate actuating components, the one back driving the other and any of the other's relevant associated transmission mechanism components).

In one optional implementation, reciprocating element 4 is coupled to transmission mechanism 103 via a wrist 104. Transmitting force and/or torque through a wrist mechanism or flexible shaft, as described above, is known to persons familiar with robotics and powered medical device design. For example, a bendable band may be pushed and pulled through a single degree of freedom (DOF) wrist, a cable (e.g., a Bowden cable or the like) may be pushed and pulled through a two-DOF wrist, and a flexible torque tube may be used to transmit torque through a one- or two-DOF wrist. Exemplary structures and methods for transmitting force and/or torque through a wrist are described, for example, in U.S. Patent Application Publication No. 2012/0215220, entitled "Fusing and Cutting Surgical Instrument and Related Methods" (filed Feb. 17, 2012); U.S. Pat. No. 7,303,107 B2, entitled "Surgical Stapling Apparatus" (filed Jul. 19, 2006); U.S. Pat. No. 7,784,662 B2, entitled "Surgical Instrument with articulating shaft with a single pivot closure and double pivot frame ground" (filed Apr. 7, 2005); and U.S. Pat. No. 7,861,906 B2, entitled "Surgical stapling apparatus with articulatable components" (filed Feb. 14, 2008), all of which are incorporated herein by reference in their entireties.

As shown in FIG. 2, computer control system 101 receives at least two inputs 105_a_, 105_b_ that result in motion of reciprocating element 4. For example, in one exemplary implementation a first input 105*a*, is a pincer type grip master control that when activated moves reciprocating element 4 slave to open and close jaws 1*a* and 1*b* as described above with reference to FIGS. 1A to IC. Computer control system 101 prevents any input from first input 105*a* from commanding actuator 102 to move reciprocating element 4 to a position distal from the position shown in FIG. 1C, so that operator control via first input 105*a* will not result in inadvertent cutting of tissue between jaws 1*a*, 1*b*. This feature is a key safety aspect, since with purely mechanical implementations if the reciprocating element mechanical limit stop 12 is mistakenly out of position, tissue may be cut when only grasping between jaws 1*a*, 1*b* is intended.

Therefore, in accordance with an aspect of the present disclosure, the user activates second input 105*b* in order to move reciprocating element 4 into gap 10 and cut tissue, as illustrated in FIGS. 1D and 1E. Second input 105*b* is, for example, a foot pedal. In some implementations, an optional third input 105*c* is included in system 100. Details concerning various input device configurations (e.g., inputs 105) are described below.

FIG. 2 also shows an Electrosurgical Unit (ESU) 106 coupled to electrodes 107 on jaws 1*a*, 1*b*. In some implementations, as shown, ESU 106 is coupled to computer control system 101 so that ESU 106 receives commands via inputs 105*a*, 105*b*, and optionally 105*c*, to introduce electrosurgical energy to electrodes 107. In other implementations, ESU 106 and electrodes 107 are separate from system 100, and inputs received for computer control system 101 have no control over ESU 106. In such implementations, one or more separate ESU inputs 108 (e.g., foot pedal control) are used to operate ESU 106. Thus, ESU 106 can be controlled cither from its individual control input or via the system computer (computer control system 101) in response to a system input.

Figure 3:
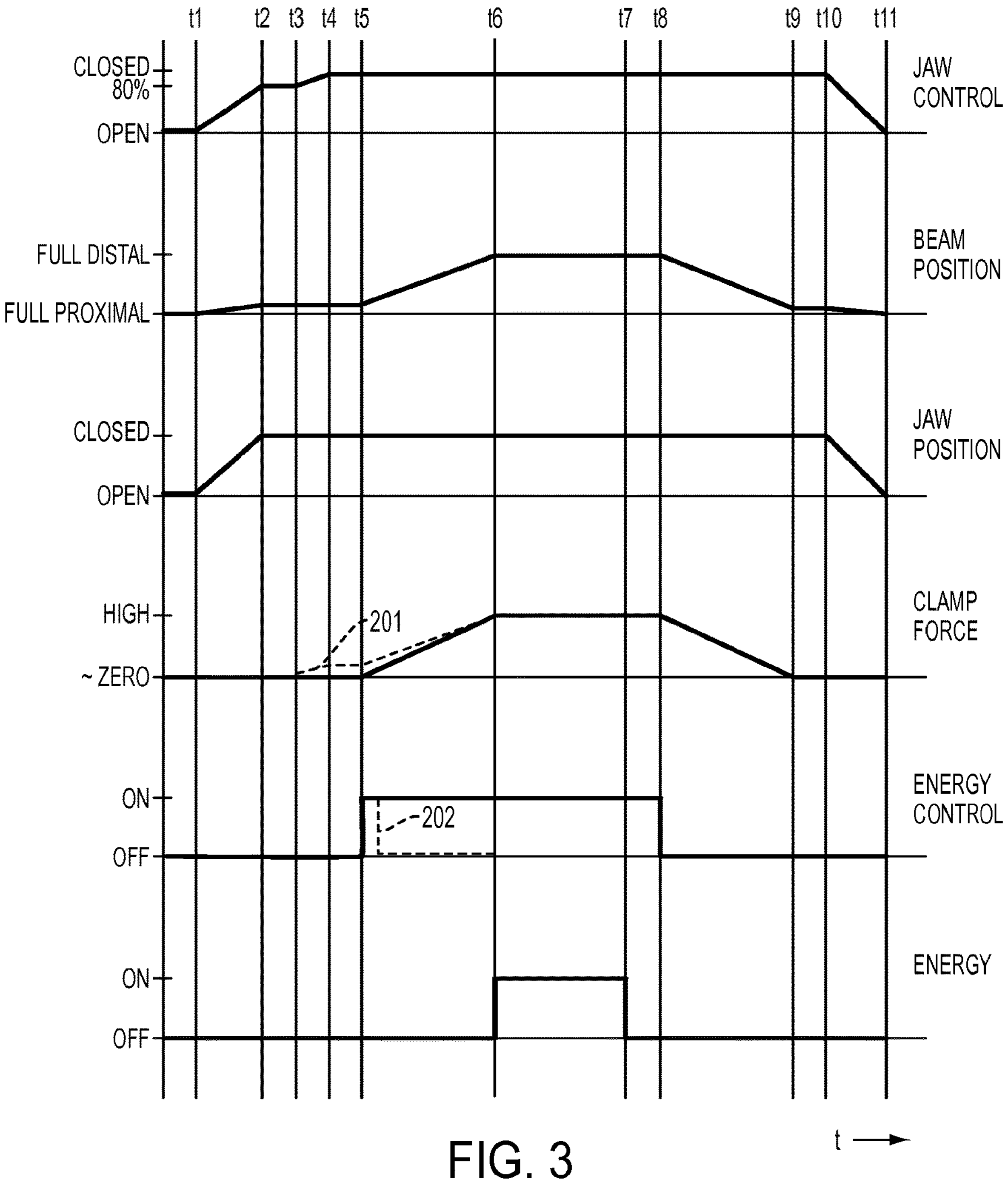
FIG. 3 is a diagram that illustrates an implementation of a process in accordance with the present teachings.

FIG. 3 is a diagram that illustrates an implementation of a process in accordance with an aspect of the present disclosure. Six conditions are shown from top to bottom: jaw position control, reciprocating element (beam) position, jaw position, jaw clamp force, energy application control, and energy application. This process, and the ones illustrated in FIGS. 4 and 5, along with the variations described herein, can be implemented in various systems ranging, for example, from large, general purpose, computer-controlled teleoperated surgical robots to hand-held, single purpose, computer-controlled surgical tools. As this process is described, various alternative implementations are also described.

At t1 an operator begins to operate a jaw position control (e.g., first input 105*a*). This control is typically operated by one or more digits of the hand as an emulation of control of a purely hand-operated instrument, such as a small forceps. For example, in one surgical robotic system, the jaw position is controlled by the operator squeezing pincer elements together with two digits. Alternatively, a digit-operated trigger, a foot pedal, or other control input may be used. Similar control may be implemented in a hand-held tool, which may use a trigger or hand grip function to control the jaw position.

As the operator begins to move the jaw position control towards the jaw closed position, the reciprocating element 4 moves slightly in the distal direction. As described above, this distal direction movement moves the jaws from the open position to the closed position. As shown in FIG. 3, at t2 the jaw position control has been moved to command the jaws to fully close, the reciprocating element has moved slightly in the distal direction, and the jaws move to a fully closed position in which tissue to be sealed and cut is held between the jaws.

As also shown, at t2 the clamping force on tissue held between the jaws is shown to be substantially zero (~zero). In fact, the tissue is held between the jaws at a light pinching force sufficient to keep the tissue from sliding between the jaws. For purposes of this description, the clamping force is considered to be ~zero. It will be understood, however, that even at this light holding force, electrosurgical energy may be applied to begin to fuse the tissue.

Further shown at t2, the jaw position control is not fully closed. Instead, full jaw closure is commanded when the jaw control is closed to an intermediate position, such as about eighty percent (80%) closed. In certain implementations, reserving a small amount of jaw position control motion is a key feature that provides the operator with a small amount of haptic feel, allows the operator to control a small amount of additional clamping force, or provides a safety margin that must be crossed to continue with the process. In optional implementations, however, jaw position control and jaw position are correlated so that one hundred percent (100%) jaw position control closure is required to fully close the jaws. Details on reservation of jaw control are described, for example, in U.S. patent application Ser. No. 13/655,999, entitled "Grip Force Control for Robotic Surgical Instrument End Effector" (filed Oct. 19, 2012), which is incorporated herein by reference in its entirety.

In accordance with an aspect of the present disclosure, the operator is free to control jaw position within the range illustrated by the conditions at t1 and t2 without concern that the reciprocating element will cut tissue that is between the jaws. The reciprocating element will move distally a sufficient amount to begin to cut tissue between the jaws only when at least a second condition occurs, so that a combination of at least two conditions is required before tissue cutting occurs, and the second condition is more than a mere safety release condition.

At t3 the operator begins to close the jaw position control the remaining twenty percent (20%), so that at t4 the jaw position control is fully closed. In some implementations, this further jaw position control closure has no effect on the reciprocating element position, jaw position, or clamping force. In alternative implementations, however, this small control motion moves the reciprocating element slightly more distally, which in turn begins to apply a light clamping pressure to tissue between the jaws. This situation is illustrated in dashed line at 201. In implementations in which jaw position control and jaw position are correlated, the full jaw position control closure may command either a substantially zero clamping force or a small amount of clamping force. In accordance with an aspect of the present teachings, therefore, the operator is still free to control jaw position within the range of being fully open to applying a small clamping force without concern that the reciprocating element will cut tissue that is between the jaws.

In some optional implementations, the fully closed (or reaching another closure threshold, such as ninety-five percent) jaw position control condition is required as a safety threshold before the computer control system 101 will allow the reciprocating element 4 to move a sufficient distance to begin to cut tissue between the jaws.

In various optional implementations, if at any time prior to t5 the jaw position control is moved to open the jaws, the jaws will open.

At t5, with the tissue to be sealed and cut between the jaws, the operator gives the command to apply energy (e.g., second input 105*b* or a separate input directly associated with ESU 106), which is effectively a command to seal and cut the clamped tissue. An example of such a command is the operator pressing or otherwise actuating an input device such as a foot pedal or button (e.g., one color-coded yellow in accordance with industry standards). As shown in FIG. 3, when the energy control command is received, the reciprocating element is moved to its full distal position so that a high force clamp is applied to tissue between the jaws. By the nature of the design, it can be seen that as the high force clamp is applied, tissue between the jaws is cut. At t6 the reciprocating element is at its full distal position, high force clamp is applied to the tissue, and the tissue has been cut by the reciprocating element.

In the depicted implementation, at t6 electrosurgical energy is automatically applied to electrodes in the jaws to fuse the tissue clamped between the jaws. The electrosurgical energy is applied until tissue fusion is sensed (as is known in the art) at t7, at which time the energy is removed. Consequently, at t7 the clamped tissue has been cut, and the tissue on either side of the cut has been fused.

As shown in FIG. 3, the reciprocating element remains at its distal-most position (the full distal position) until the energy control input is returned to the off position. When at t8 the energy control input is moved to the off position, the reciprocating element is automatically moved distally so that at t9 the reciprocating element is at a near full proximal position, the clamp force returns to substantially zero, and the jaws remain closed. Then, to open the jaws, at t10 the operator opens the jaw position control, the reciprocating element moves to its full proximal position, and the jaws fully open, as shown at t11. At this position, in one implementation the system 100 is then ready to perform one or more subsequent tissue fusing and sealing operations, or tissue grasping operations, as described herein.

In addition to the illustrative implementation and the variations described above, many additional variations may be applied in other implementations. The options described above and below may be combined in any way practical, as long as one or more particular option does not prevent the implementation of an embodiment with one or more other options. These various options apply to both relatively larger teleoperated surgical robots designed to operate a variety of surgical tools and to relatively smaller hand-held surgical tools designed to operate as a dedicated single instrument type.

As described above, the cutting and fusing actions are combined with the actuation of a single input, such as a foot pedal or button. Alternatively, however, the cutting and fusing actions may be separately controlled. Such separate control gives the operator the capability to cut clamped tissue without any tissue fusion taking place (a so-called “cold cut”). If tissue fusion is desired, then a second control is operated, such as a second foot pedal or button. For example, to implement cutting, a blue-colored foot pedal or button is pressed (e.g., second input 105*b* is provided), and to implement tissue fusion, a yellow-colored foot pedal or button is pressed (e.g., third input 105*c* or an input directly associated with ESU 106 is provided). As an alternative to foot pedals or buttons, various other devices may be used to input the cut and fuse commands, such as a switch positioned near the jaw position control input, a voice command, etc. A key advantage, however, is that the input device used to control the cutting function (e.g., second input 105*b*) is separate from the device used to control the jaw position and tissue clamping force (e.g., first input 105*a*). Thus, even though a single reciprocating element is used to both actuate jaw position and carry out tissue cutting, two different input devices are used to control these two functions. These separate inputs prevent an inadvertent over-actuation of the jaw position control input, as may occur when a reciprocating element limit switch has been incorrectly positioned, and unwanted tissue cutting.

In some instances the two (or more) separate inputs are combined in a single type of input device. This single type of input device travels over a first range of motion to command jaw position, and it travels over a second range of motion or moves to a second position outside the first range of motion to control cutting. For example, the reciprocating element's first range of motion, which controls jaw opening and closing, may be controlled by a first range of motion of a spring-loaded pincer mechanism pinched by digits of the hand. The reciprocating element's second range of motion, which is associated with tissue cutting, is then controlled by a second range of motion of the pincer mechanism. This second range of motion is separated from the first range of motion by a clear divider, such as a noticeably higher spring force, a noticeable haptic detent, etc. Elements having two controllable ranges of motion are described, for example, in U.S. patent application Ser. No. 13/655,999, entitled “Grip Force Control for Robotic Surgical Instrument End Effector” (filed Oct. 19, 2012), which is incorporated herein by reference in its entirety. Similarly, a spring-loaded foot pedal may have two clearly divided ranges of motion, or an input may be difficult to move into a second operating position or direction (akin to a reverse gear “lockout” feature in some automobile manual transmissions), or a second mechanical input must be held in order to move the first input into the second range or position (akin to button that must be pressed on an automobile automatic transmission position selection lever). A key feature is still that while the input is operated to control jaw position, inadvertent tissue cutting is prevented, since the input cannot move into the second range of motion or position without a positive action by the operator each time a transition to the second range of motion or position is desired.

Whether a single input is used to control both cutting and fusing, or whether separate inputs are used, the required input may be continuous, such as holding a spring loaded pedal or button in an ON position, or the input may be a brief pulse that starts the function. If the cutting and scaling functions are combined, then a single tap of a foot pedal or button may be used to start the cutting and sealing process between t5 and t7 as shown in dashed line at 202. Likewise, a single tap on one foot pedal may start the cutting function and a single tap on a second pedal may start the fusing function. Control logic prevents the fusing function from beginning if the second pedal is tapped before the reciprocating element is in the correct full distal position. A combination of a tap on one input and a continuous hold on another input may be used. An optional warning (audio, video) may be output that advises the operator that the fusing function has not started. If a tap is used to control the tissue cutting function alone, then the reciprocating element may automatically return to the full- or near-proximal position after the cutting, or a second input, such as a second tap or the opening of the jaw position control, may be used to return the reciprocating element to the full- or near-proximal position.

As a safety feature, moving the jaw position control towards open (e.g., opening the grip control) at any time during the process may stop a portion or all of the process implemented up to that time. For example, if the jaw position control is opened mid-way through the tissue cutting function, the reciprocating element is returned to its full- or near-proximal position and the jaws are moved to an open position. The operator then manages any bleeding or other effect of the cutting. Likewise, if the jaw position control is opened mid-way through the tissue fusing function, the electrosurgical energy is removed from the electrodes so that the fusing function stops, and the reciprocating element returns to its full- or near-proximal position, either automatically or as the result of another control input.

Similarly, if the combined or individual cutting and fusing functions are controlled by a continuous input, such as a continuous foot pedal or button press, releasing the input may stop the cutting or fusing function and variously keep the reciprocating element in place or automatically returning the reciprocating element to its full- or near-proximal position.

In some implementations, the control system outputs an indication that the cut function and/or the fusing function are complete and indicated successful. In such implementations, if a situation occurs in which the correct conditions to carry out the cutting or the sealing function has occurred, but the expected indication is not output to the operator so that the operator suspects the function was not successful, or if the system outputs a second indication that the expected function was unsuccessful, various approaches may be used. Exemplary user interface systems providing information regarding an actual or expected outcome of a computer-controlled surgical process are described in, for example, U.S. Patent Application Publication No. 2012/0248167, entitled "Methods and Systems for Detecting Staple Cartridge Misfire or Failure" (filed May 15, 2012); U.S. Patent Application Publication No. 2012/0209314, entitled "Methods and Systems for Indicating a Clamping Prediction" (filed Jan. 13, 2102); U.S. Patent Application Publication No. 2012/0205419, entitled "Methods and Systems for Detecting Clamping or Firing Failure" (filed Jan. 13, 2012); and U.S. Patent Application Publication No. 2012/0209288, entitled "Indicator for Knife Location in a Stapling or Vessel Sealing Instrument" (filed Jan. 13, 2012), all of which are incorporated by reference herein in their entireties.

For example, if the operator suspects or receives an indication that the tissue cutting function was unsuccessful, the system may be configured to permit the operator to attempt the cutting function again, or to prevent the operator from attempting the cutting function again, or to limit the number of subsequent attempted cutting functions. To recover from an unsuccessful cutting situation, the system may be variously configured as described above to have the reciprocating element move to the full- or near proximal position so that the jaws can be opened.

Similarly, if the operator suspects or receives an indication that the tissue fusing function was unsuccessful, the system may be configured to permit the operator to attempt the fusing function again, or to prevent the operator from attempting the fusing function again, or to limit the number of subsequent attempted fusing functions. To recover from an unsuccessful fusing situation, the system may be variously configured as described above to have the electrosurgical energy removed from the jaws and the reciprocating element move to the full- or near proximal position so that the jaws can be opened.

If at any time the reciprocating element is commanded to return to a full proximal position so that tissue may be removed from the jaws, but the full proximal position is not sensed, the control system may output a warning to the operator that indicates that the reciprocating element is stuck in an intermediate position. The system may be configured to attempt to recover by automatically moving the reciprocating element distally and then once again to move proximally in an attempt to achieve the full proximal position, or by dithering the reciprocating element while urging it towards the full proximal position, or by allowing the operator to attempt to move the reciprocating element by moving an input device, such as the device used to initiate the cut function.

Figure 4:
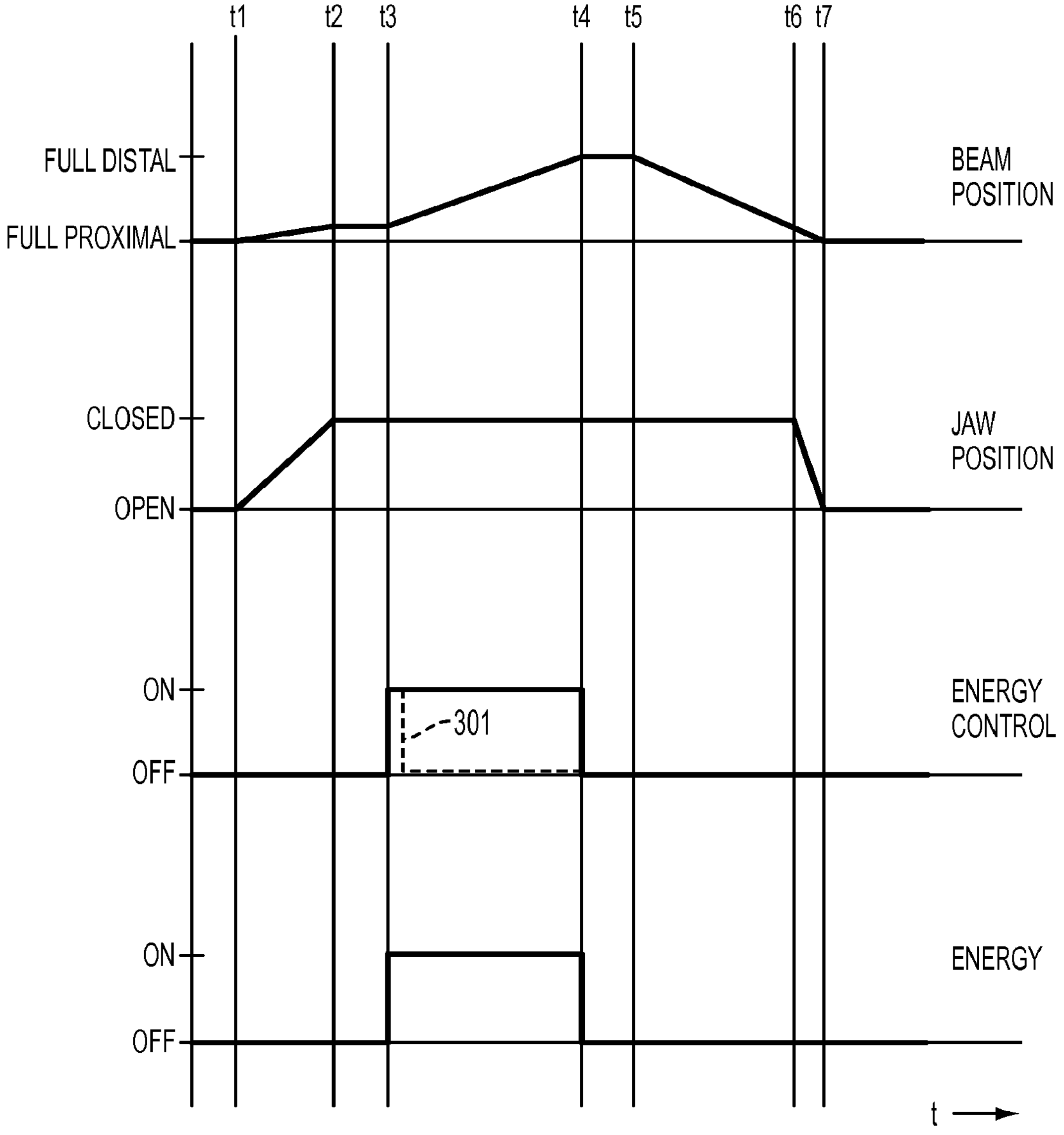
FIG. 4 is a diagram that illustrates an implementation of an alternative process, in accordance with the present teachings.

FIG. 4 is a diagram that illustrates an implementation of another process in accordance with an aspect of the present disclosure. Four conditions are illustrated from top to bottom: reciprocating element (beam) position, jaw position, energy application control, and energy application. Jaw position control and clamp force are as described above and omitted for clarity.

As shown in FIG. 4, between times t1 and t2 the beam position and jaw position are related as described above. At t3, the operator initiates electrosurgical tissue fusing energy application. This initiation is started by operating a second control system input (e.g., input 105*b*), other than the input normally used to control jaw position during the tissue grasping function. The energy control may be held in an ON position as shown in FIG. 4, or alternatively may be a short pulse or tap on the input, as shown in dotted line 301. For example, the operator may press and hold a foot pedal, or the operator may tap the foot pedal.

In response to the operator initiating energy application, the control system commands the ESU to apply energy to the electrodes and commands the actuator to move the reciprocating element towards the distal-most position. Thus electrosurgical tissue fusing energy is applied as the reciprocating element moves distally over the jaws. In addition, tissue cutting occurs as the tissue is fused, so that bleeding is controlled. At t4, the reciprocating element is at its full distal position, tissue fusing is complete (as indicated by the ESU), and energy is removed from the electrodes.

At t5 the jaws are commanded to open, either by the operator using the jaw position control input, or automatically by the control system. As the reciprocating element returns to its full proximal position and at t6 passes the near-proximal position as described above, the jaws start to open. At t7 the beam has returned to its full proximal position and the jaws are open.

As described herein, in some instances the control system may be configured to allow the operator to interrupt the fusing and cutting action, so that if the foot is lifted from a foot pedal, or if the jaws are commanded to open by using the jaw position control input, energy application is stopped and the reciprocating element is returned to the proximal or near-proximal position.

Figure 5:
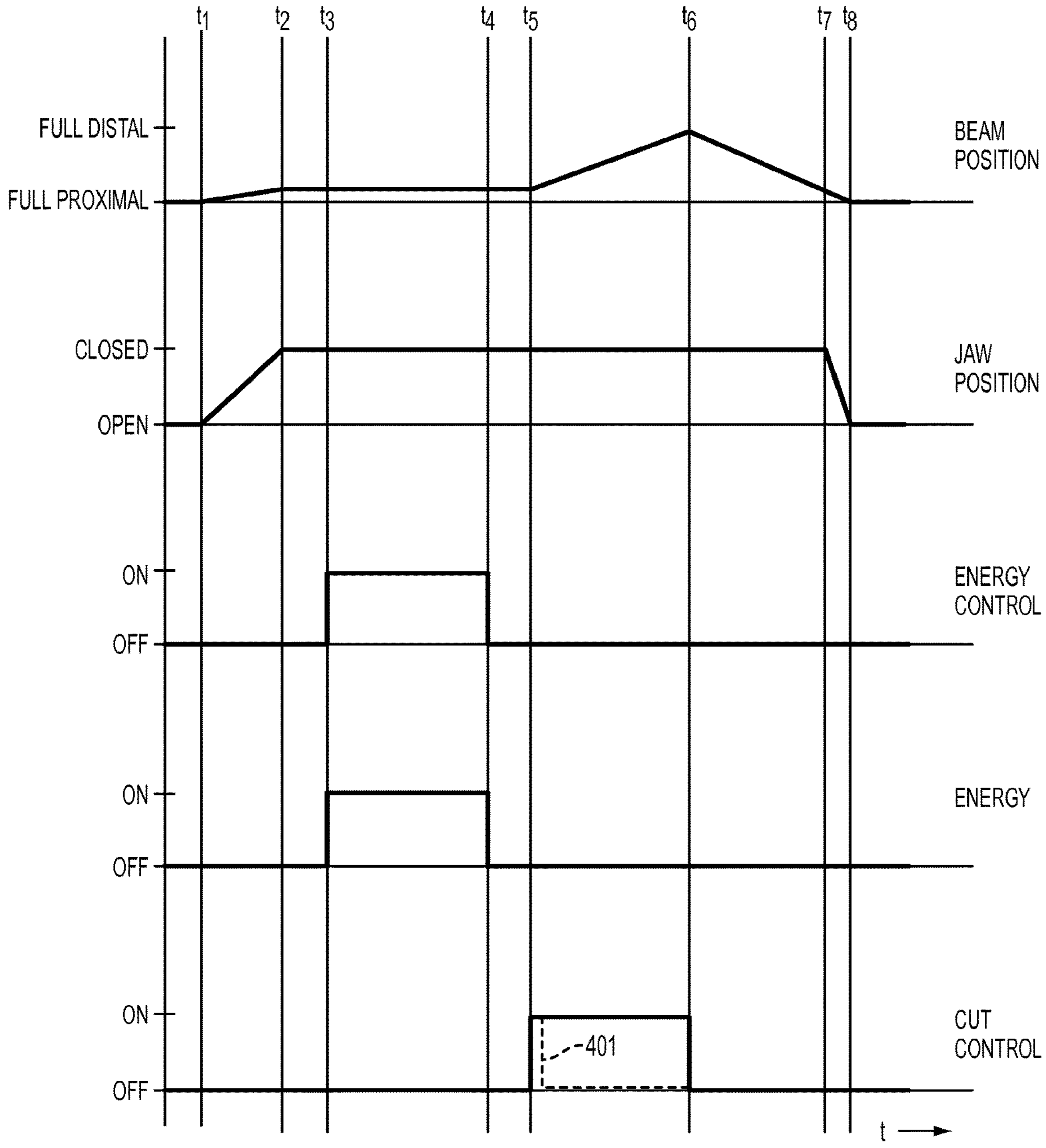
FIG. 5 is a diagram that illustrates an implementation of another alternative process, in accordance with the present teachings.

FIG. 5 is a diagram that illustrates an implementation of yet another process in accordance with an aspect of the present disclosure. Five conditions are illustrated from top to bottom: reciprocating element (beam) position, jaw position, energy application control, energy application, and tissue cutting control. Jaw position control is as described above and omitted for clarity. FIG. 5 illustrates an implementation in which tissue fusing and tissue cutting are separately controlled.

As shown in FIG. 5, between t1 and t2 the reciprocating element position and jaw position are related as described above. At t2 and at t3, the tissue is lightly clamped by the reciprocating element being positioned at the near-proximal position. In some instances, this light clamping is sufficient to allow effective tissue fusing, and show tissue fusing energy application is started at t3. The reciprocating element does not move during the energy application. At t4 the tissue fusing is complete and the energy is removed.

At t5 the operator commands the tissue cutting function to begin. The reciprocating element moves to its distal-most position at t6. As shown, in some instances the reciprocating element moves as long as a cut control input command is received. In other instances, a short pulse initiates the tissue cutting function, as shown in dashed line at 401. From t6 to t8 the reciprocating element returns to its proximal position, either automatically from a control system command or by the operator commanding the jaws to open.

It can be seen that since the tissue fusing and cutting functions are separately controlled, tissue cutting alone can be performed (the cold cutting referred to above).

Further, as described above, the separately controlled tissue fusing and cutting functions may be operated by two separate input devices, or they may be operated by two unique and distinct control functions on the same input device. For example, if a single foot pedal is used to control both tissue fusing and cutting, a single tap or a continuous hold-down may be used to control energy application, and a double tap may be used to command tissue cutting (or vice-versa). It can be appreciated, therefore, that many combinations of one or more input devices (hand operated, foot operated, head operated, elbow or knee or other body part operated, voice operated, eye gaze operated, operated by a second person, etc.) the or each input device providing one or more distinct ranges of motions or positions, can be used to safely and separately control the grasping function versus the fusing function, the cutting function, or the combined fusing and cutting function.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well, with powered or hand-actuated actuation of the various inputs.

Other embodiments in accordance with the present disclosure will be apparent to those skilled in the art from consideration of the specification and practice of the teachings disclosed herein. It is intended that the specification and examples be considered as exemplary only, with a true scope and spirit being indicated by the following claims.

What is claimed is:

1. A control system for controlling an end effector of a medical instrument, the control system comprising:

a processor communicatively coupled with a first user-actuated input mechanism and a second user-actuated input mechanism, the processor configured to:

in response to a first input at the first user-actuated input mechanism:

command a jaw mechanism of the end effector, the jaw mechanism moveable through a range of motion between an open position and a close position, to move from an open position to an intermediate closed position within the range of motion of the jaw mechanism, and command a translating mechanism of the end effector, the translating mechanism moveable between a proximal position and a distal position relative to the jaw mechanism, to move from a proximal position to an intermediate position relative to the jaw mechanism; and in response to a second input at the first user-actuated input mechanism:

command the jaw mechanism to move to the closed position, and command the translating mechanism of the end effector to move from the intermediate position to the distal position.

2. The control system of claim 1, wherein the processor is further configured to:

await a third input at the second user-actuated input mechanism before commanding the jaw mechanism and the translating mechanism in response to the second input at the first user-actuated input mechanism.

3. The control system of claim 2, wherein the first and second inputs comprise actuation of a trigger mechanism or pincer elements, and wherein the third input comprises depression of a button or a foot pedal.

4. The control system of claim 1, wherein the processor is further configured to, in response to a third input at the first user-actuated input mechanism after the second input, command the translating mechanism to move from the distal position to the proximal position.

5. The control system of claim 4, wherein the processor is further configured to, in response to a fourth input at the first user-actuated input mechanism, command the jaw mechanism to move from the closed position to the open position.

6. The control system of claim 1, wherein the processor is further configured to provide feedback in response to the translating mechanism moving from the intermediate position to the distal position.

7. The control system of claim 1, wherein the processor is further configured to provide feedback indicating a clamping force of the jaw mechanism.

8. The control system of claim 7, wherein the feedback comprises haptic feedback.

9. The control system of claim 1, wherein the processor is further configured to vary a clamping force of the jaw mechanism in response to the first input at the first user-actuated input mechanism.

10. The control system of claim 1, wherein the processor is further configured to prevent movement of the translating mechanism from the intermediate position to the distal position relative to the jaw mechanism in absence of receiving both the second input and a third input at the second user-actuated input mechanism, wherein the third input occurs before the second input.

11. The control system of claim 1, wherein:

the processor is communicatively coupled to a third user-actuated input mechanism; and the processor is further configured to command actuation electrodes of the jaw mechanism to deliver fusing energy in response to a third input at the third user-actuated input mechanism.

12. A method for controlling an end effector of a medical instrument, the method comprising:

receiving a first input at a first user-actuated input mechanism;

in response to receiving the first input at the first user-actuated input mechanism:

commanding a jaw mechanism of an end effector, the jaw mechanism having a range of motion between an open position and a closed position, to move from the open position to an intermediate closed position within the range of motion of the jaw mechanism, and commanding a translating mechanism of the end effector, the translating mechanism having a range of motion between a proximal position and a distal position relative to the jaw mechanism, to move from the proximal position to an intermediate position relative to the jaw mechanism;

receiving a second input at the first user-actuated input mechanism; and in response to receiving the second input:

commanding the jaw mechanism to move to the closed position, and commanding the translating mechanism of the end effector to move from the intermediate position to the distal position.

13. The method of claim 12, wherein the second input occurs after a third input at a second user-actuated input mechanism.

14. The method of claim 13, further comprising preventing movement of the translating mechanism from the intermediate position to the distal position relative to the jaw mechanism in absence of receiving both the second input and the third input.

15. The method of claim 13, further comprising:

receiving a fourth input, after receiving the second input, at the first user-actuated input mechanism; and in response to receiving the fourth input, commanding the translating mechanism to move from the distal position to the proximal position.

16. The method of claim 13, wherein:

receiving the first and the second input at the first user-actuated input mechanism comprises receiving input at one of a trigger mechanism or pincer elements, and receiving the third input at the second user-actuated input mechanism comprises receiving input at one of a button or a foot pedal.

17. The method of claim 12, wherein receiving the second input comprises performing a continuous input at the first user-actuated input mechanism.

18. The method of claim 17, further comprising:

removing the continuous input at the first user-actuated input mechanism; and moving the jaw mechanism to an open position in response to removing the continuous input.

19. The method of claim 12, wherein:

commanding the jaw mechanism of the end effector to move from the open position to an intermediate closed position within the range of motion further comprises commanding the jaw mechanism to provide a first clamping force, and commanding the jaw mechanism to move to the closed position further comprises commanding the jaw mechanism to provide a second clamping force, wherein the second clamping force is greater than the first clamping force.

20. The method of claim 12, further comprising:

receiving a third input at a third user-actuated input mechanism; and in response to receiving the third input, commanding electrodes of the jaw mechanism to deliver fusing energy.

* * * * *